United States Patent [19]

Bortinger

[11] Patent Number: 5,296,436
[45] Date of Patent: Mar. 22, 1994

[54] PHOSPHOROUS/VANADIUM OXIDATION CATALYST

[75] Inventor: Arie Bortinger, Ridgewood, N.J.

[73] Assignee: Scientific Design Company, Inc., Little Ferry, N.J.

[21] Appl. No.: 2,240

[22] Filed: Jan. 8, 1993

[51] Int. Cl.$^5$ .................. B01J 27/198; B01J 27/19; C07D 307/34

[52] U.S. Cl. .................. 502/209; 502/211; 549/259; 549/260

[58] Field of Search .......................... 502/209

[56] References Cited

U.S. PATENT DOCUMENTS

| 3,980,585 | 9/1976 | Kerr et al. | 252/437 |
|---|---|---|---|
| 4,017,521 | 4/1977 | Schneider | 260/346.8 A |
| 4,043,943 | 8/1977 | Schneider | 252/437 |
| 4,056,487 | 11/1977 | Kerr | 252/435 |
| 4,105,586 | 8/1978 | Kerr | 252/437 |
| 4,147,661 | 4/1978 | Higgins et al. | 252/435 |
| 4,418,003 | 11/1983 | Udovich et al. | 502/209 |
| 4,515,899 | 5/1985 | Click et al. | 502/35 |
| 4,515,904 | 5/1985 | Edwards | 502/209 |
| 4,632,915 | 12/1986 | Keppel et al. | 502/209 |
| 4,668,652 | 5/1987 | Feimagalli et al. | 502/209 |
| 4,670,415 | 6/1987 | Keppel et al. | 502/209 |
| 5,070,060 | 12/1991 | Barone | 502/209 |
| 5,158,923 | 10/1992 | Barone | 502/209 |

FOREIGN PATENT DOCUMENTS 0466480  3/1992  European Pat. Off. .

Primary Examiner—Paul E. Konopka
Attorney, Agent, or Firm—Kenneth H. Johnson

[57] ABSTRACT

An improvement in the oxidation catalyst used for the partial oxidation of n-butane and containing vanadium and phosphorus, zinc, lithium and molybdenum mixed oxides which comprises adding the molybdenum as a compound which is dissolved in a solvent during the manufacture of the catalyst.

23 Claims, No Drawings

PHOSPHOROUS/VANADIUM OXIDATION CATALYST

BACKGROUND OF THE INVENTION

The present invention relates to an improved PVO-zinc activated, lithium modified catalyst containing an oxide of molybdenum for use the in the partial oxidation of hydrocarbons to prepare dicarboxylic acids and anhydrides. Most particularly, the invention relates to the preparation of the improved molybdenum containing catalyst.

Basically, all of the methods used to prepare oxidation catalysts seek to obtain vanadium in a valence state of less than +5. One method of achieving this is to begin with vanadium in less than the +5 valence state. Another method and that used most widely in the art is to start with vanadium in the +5 state and reduce the valency to less than +5. This invention relates to the latter method. Several variations on this method have been used to obtain these catalyst. In one method $V_2O_5$ is reduced in a solution with HCl to obtain vanadyl chloride. A typical catalyst preparation may involve dissolving the vanadium, phosphorus, and other components in a common solvent. The reduced vanadium with a valence of less than 5 is obtained by initially using a vanadium compound with a valence of plus 5 such as $V_2O_5$ and thereafter reducing to the lower valence with for example, hydrochloric acid during the catalyst preparation to form the vanadium oxysalt, vanadyl chloride, in situ. The vanadium compound is dissolved in a reducing solvent, such as hydrochloric acid, which solvent functions not only to form a solvent for the reaction, but also to reduce the valence of the vanadium compound to a valence of less than 5. Preferably, the vanadium compound is first dissolved in the solvent and thereafter the phosphorus and other components, if any, are added. The reaction to form the complex may be accelerated by the application of heat. The complex formed is then, without a precipitation step, deposited as a solution onto a carrier and dried. Generally, the average valence of the vanadium will be between about plus 2.5 and 4.6 at the time of deposition onto the carrier.

In another method the catalyst is prepared by precipitating the metal compounds, either with or without a carrier, from a colloidal dispersion of the ingredients in an inert liquid. In some instances the catalyst may be deposited as molten metal compounds onto a carrier. The catalysts have also been prepared by heating and mixing anhydrous forms of phosphorus acids with vanadium compounds and other components. In any of the methods of preparation, heat may be applied to accelerate the formation of the complex.

A method of obtaining vanadyl chloride was disclosed by Koppel et al, Zeit. anorg. Chem, 45, p. 346–351, 1905 by the reduction of $V_2O_5$ in alcoholic HCl solution. This method has been recommended for the preparation of the phosphorus-vanadium oxidation catalyst for example, by Kerr in U.S. Pat. No. 3,255,211 where the solvent also serves as the reducing agent. Subsequently, U.S. Pat. No. 4,017,521; 4,043,943; 4,251,390; 4,283,307 and 4,418,003 for example, employed this method generally referred to as the "anhydrous process" of reducing vanadium to prepare the basic phosphorus-vanadium catalyst. The catalysts produced by this latter method have been found to be generally superior to similar catalyst by the other methods. Specifically what had occurred to this class of oxidation catalysts prior to the return to the anhydrous process had been the addition of a veritable cornucopia of elements to the base vanadium-phosphorus composition, see for example U.S. Pat. No. 4,105,586 where in addition to V, P and O the catalyst must contain nine other elements. The catalyst were satisfactory, but manufacturing was difficult because of the number of components and their varying effects on the catalyst performance.

Many references disclose oxidation catalysts which are suitable for producing maleic anhydride by the partial oxidation of n-butane, which catalysts contain molybdenum as one component of a phosphorus, vanadium mixed oxide catalyst. For example U.S. Pat. No. 3,980,585 discloses a catalyst containing P, V Cu and one of Te, Zr, Ni, Ce, W, Pd, Ag, Mn, Cr, Zn, Mo, Re, Sn, La, Hf Ta, Th, Ca, U or Sn; and U.S. Pat. No. 4,056,487 discloses a PVO catalyst containing Nb, Cu, Mo, Ni, Co and plus one or more of Ce, Nd, Ba, Hf, U, Ru, Re, Li or Mg. U.S. Pat. No. 4,515,904 discloses a procedure for preparing PVO catalysts which may include one metal of Mo, Zn, W, U, Sn, Bi, Ti, Zr, Ni, Cr or Co in atomic ratios of metal: V of 0.001 to 0.2:1.

U.S. Pat. No. 4,147,661 discloses high surface area PVO mixed oxide catalyst additionally containing W, Sb, Ni and/or Mo at atomic ratios of 0.0025 to 1:1 to vanadium.

U.S. Pat. No. 4,418,003 discloses PVO catalysts containing either Zn or Mo which is deactivated by Na or Li and which may also contain Zr, Ni, Ce, Cr, Mn, Ni ana Al.

Commonly assigned U.S. Pat. No. 5,070,060 discloses an oxidation catalyst which contains molybdenum which is substituted for some of the phosphorous and produces a more stable catalyst.

In all of the disclosed molybdenum containing catalysts the molybdenum and any other metal are added as the oxide or salt of the metal directly to the reaction mixture during formation of the catalyst. While some of the metal compounds, especially the chloride salts, are readily dissolved in the reaction mixture, the molybdenum oxide does not dissolve well and is not fully dispersed in the catalyst.

It is a feature of the present invention that better dispersion of the molybdenum throughout the catalyst is obtained which results in higher conversions and selectivities.

SUMMARY OF THE INVENTION

The present invention lies in an improvement in the phosphorus/vanadium/zinc/lithium/molybdenum
mixed oxide oxidation catalyst. The present catalysts are produced by the process comprising reducing vanadium in the +5 valence state in a substantially anhydrous organic medium to a valence of less than +5 and digesting said reduced vanadium in concentrated phosphoric acid wherein the improvement comprises adding the molybdenum compound in a solution which mixes readily with the organic medium or the phosphoric acid. The solution containing the molybdenum may be added prior to the digesting. The solvent containing the molybdenum compound may either be an organic solvent, such as an alcohol, or water. The mole ratio of the molybdenum compound to vanadium is in the ranges of 0.005 to 0.10:1, preferably 0.01 to 0.050:1 thereby obtaining an easily activated catalyst having superior resistance to deactivation by impurities and excessive heat during use and higher and longer productivity. Suitable dried catalysts have a crystallinity of 30 to 90%, preferably at least 40%.

PREFERRED EMBODIMENTS

In a preferred embodiment the improved catalyst is that produced from an alcoholic solution reduction of vanadium pentoxide wherein the organic solvent is an alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It is preferred that the reduction temperature should be maintained at no greater than 60° C. and preferably less than 55° C. Optimally active catalyst are the result when the reduction is carried out at temperatures in the range of about 35° C. to 55° C., preferably 37° C. to 50° C.

Generally in the catalyst preparation from 2500 to 4400 ml of alcohol, preferably 2700 to 4200 ml per pound of $V_2O_5$ and from 1.5 to 3.0 pounds of HCl per pound of $V_2O_5$ are employed.

To obtain the mixed oxides of vanadium and phosphorus, phosphoric acid of approximately 99% $H_3PO_4$ (98 to 101%) is added, for example, prepared from 85 $H_3PO_4$ and $P_2O_5$ or commercial grades of 105 and 115% phosphoric acid diluted with 85% $H_3PO_4$ or water to the final required concentration of $H_3PO_4$ and the vanadium compound digested which is discerned by a change in the color of the solution to a dark blue green. The alcohol is then stripped off to obtain the dried catalyst. Preferably the alcohol is stripped off in two stages to obtain the dried catalyst. Each of the two stages comprise refluxing the solvent for about 15 minutes to 180 minutes, preferably about an hour followed by stripping of about 20–85 vol % of the solvent after the first stage refluxing step and about 40–85 vol % of the solvent remaining after the second refluxing step. Solvent remaining after the two stripping steps is removed by drying under less rigorous conditions.

The digestion of the vanadium compound in the phosphoric acid is normally conducted at reflux until the color change indicated the completed digestion.

The final removal of alcohol is usually carried out in an oven at a temperature in the range of 110° to 170° C. Reduced pressure can also be applied to lower oven temperatures. Generally calcination or roasting of the dried catalyst will be at a temperature in the range of 200° to 400° C. for a sufficient period to improve the catalytic properties of the composition.

The temperatures employed are relatively low hence the term calcination may not be appropriate. In any event, heating the composition under these temperature conditions has been found beneficial. The calcination is preferably carried out to produce materials having a characteristic powder x-ray diffraction ratio.

The organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl1-heptanol, 1,2-ethanediol, glycerol, trimethylopropane, 4-methyl 2-pentanone, diethylene glycol and triethylene glycol or mixtures thereof. The alcohol is also a mild reducing agent for the vanadium +5 compound. A preferred cosolvent system comprises 2-butanol and from 5–50 vol % of the cosolvent.

Generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalyst as well as those of the prior art in the mole ration of P/V 0.09–1.3/1. Optimum ratios P/V are found to be below 1.22/1 and above 1.0/1. The stabilizing effect of Mo allows the use of less phosphorus than otherwise comparable prior art catalyst and the concomitant benefit that phosphorus loss and the resulting deactivation of the catalyst in reactor operation is reduced, i.e., longer time trend (reactivity vs hours on stream).

The lithium component is present at an atomic ratio of 0.001 to 0.15:1, Li:V.

The point at which the zinc component, lithium component and molybdenum component is added is not critical so long it is present prior to formation of the solid catalyst precipitate. This is conveniently done along with the phosphoric acid addition, thereby assuring the intimate mixing of the catalyst components.

The lithium and zinc modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, or lithium orthophosphate and the like.

The molybdenum compound is one that may dissolved in an organic solvent, as described above or water and added to the reaction mixture. The solvent containing the molybdenum compound may be added either with the other modifiers or at different time. If water is used the solvent containing the molybdenum compound is preferably added after the first digestion and prior to the second digestion. The use of a soluble molybdenum compound dissolved in a solvent according to the present invention for addition to the reaction mixture has been found to be particularly effective in dispersing the molybdenum throughout the mixture and the final dried catalyst. Some examples of suitable soluble molybdenum catalyst include phosphomolybdic acid, ammonium molybdate (VI) tetrahydrate, lithium molybdate, molybdenum tetrabromide, molybdenum trioxyhexachloride and the like.

The resultant catalyst complex is characterized as a mixed oxide, however, the structure of the complex has not been determined but may be conveniently represented by a formula such as:

$$V\ P_a\ Zn_b\ Mo_c\ Li_d\ O_x$$

a is 0.90 to 1.3, b is 0.001 to 0.15, c is 0.005 to 0.10 and d is 0.001 to 0.15. This representation is not an empirical formula and has no significance other than representing the atom ratio of the components of the catalyst. The x in fact, has no determinate value and can vary widely depending on the combinations within the complex. That there is oxygen present is known, and the $O_x$ is representative of this.

The catalyst may be employed as. pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1.0 to about 2.0 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total productivity obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitratesodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon steel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 380° C. to about 430° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

Generally the improved catalyst of the present invention is more active and operates at a lower temperature and higher weight yield than prior anhydrous process PVO catalysts.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

EXAMPLES

The method in which the catalyst is prepared is important. The following typical catalysts reparative procedures illustrate typical catalyst work up using the information discussed above.

EXAMPLE 1

Comparative

Into a 12 liter round flask equipped with a mechanical stirrer, a gas inlet tube, thermowell, Dean stark trap with a condenser, and a heating mantle were charged 3564 ml anhydrous isobutanol and 627 grams $V_2O_5$. About 3.45 lb hydrogen chloride gas was bubbled into the stirred suspension. The reaction temperature was maintained at 40°±3° C. To the resulting dark red-brown solution was added 9.3 grams anhydrous zinc chloride, 2.92 grams lithium chloride, 12.90 grams molybdenum trioxide and a solution of phosphoric acid prepared from 193.7 grams $P_2O_5$ dissolved in 590 grams of 87.5% phosphoric acid. An additional 774 ml of anhydrous isobutanol were added to the reaction mixture. Heat was supplied and about 105 ml liquid were removed before the reaction mixture was placed under reflux conditions for 1 hour. Thereafter, about 2450 ml of distillate was removed before the reaction mixture was placed under a second reflux for 1 hour. At the end of this period, the distillation was resumed and was completed after removing a total volume of 3520 ml of solvent. The thick slurry was then dried in an oven for 16 hours at 150° C. The dry cake was then crushed and calcined at 260° C. for 3 hours. The calcined powder was mixed with 3% graphite and was formed into 3/16"×3/16" tablets with a 1/16" I.D. hole struck therethrough. The calcined catalyst had 52% crystallinity and the activity is shown in TABLE I.

EXAMPLE 2

Using phosphomolybdic acid in an organic solvent

The procedures of Example 1 were followed except the molybdenum trioxide was replaced with 17.67 grams of 12-molybdophosphoric acid (phosphomolybdic acid) which were dissolved in 63 ml methanol and 124 ml isobutanol. The solution was added into the reaction mixture after the first digestion and after distilling off about 2500 ml solvent. The reaction mixture was refluxed for 30 minutes. At the end of this period the distillation was resumed and was completed after removing a total volume of solvent of 3540 ml. The thick slurry containing crystallinic material was then dried in an oven for 16 hours at 150° C. The dry cake was then crushed and calcined at 260° C. for 3 hours. The calcined powder was mixed with 3% graphite and was formed in 3/16"×3/16" tablets with a 1/16" I.D. hole struck therethrough. The calcined catalyst had 73% crystallinity. The catalytic activity is shown in TABLE I.

EXAMPLE 3

The procedures of Example 2 were followed except that the 12-molybdophosphoric acid was added with the zinc and lithium chloride salts before the addition of the phosphoric acid prior to the first digestion. Also the second reflux period was increased to 1 hour. At the end of this period, the distillation was resumed and was completed after removing a total volume of solvent of 3490 ml. The thick slurry containing crystallinic material was then dried in an oven for 16 hours at 150° C. The dry cake was then crushed and calcined at 260° C. for 3 hours. The calcined powder was mixed with 3% graphite and was formed in 3/16"×3/16" tablets with a 1/16" I.D. hole struck therethrough. The calcined catalyst had 71% crystallinity. The catalytic activity is shown in TABLE I.

EXAMPLE 4

Using phosphomolybdic acid dissolved in water

The procedures of Example 2 were followed except the 63 ml of methanol was replaced with 60 ml of water which readily dissolved the phosphomolybdic acid. The calcined catalyst had 61% crystallinity.

CATALYST EVALUATIONS

Each of the examples catalyst are tested for activity and selectivity in the n-butane partial oxidation to maleic anhydride. Air in the feed is balanced with the % butane used in the reaction.

The catalyst is conditioned for use by placing the catalyst (tablets) in the tubular reactor of a fixed bed reactor and carrying out the conditioning.

The reactor is 5 foot stainless steel tube, 1 inch outside diameter, packed with a 3.5 foot catalyst bed (3/16"×3/16" tablet with a 1/16" center hole) and with inert ¼ inch Alundum pellets on top of the catalyst material to a height 33% of the height of the catalyst. The reactors are encased in a 7% sodium nitrate; 40% sodium nitrite ; 53% potassium nitrite eutectic mixture constant temperature salt bath. The catalyst is loaded in the reactor and conditioned by a slow bring-up of the catalyst to operating temperature at the rate of 5° to 20° C. per hour achieved by heating the reactor and adjusting the gas flow from 0.5 to 1.5 mole % butane in air at an initial flow of GHSV of $900^{-1}$ hours up to $2500^{-1}$ hours while maintaining a desired conversion level, e.g., about 75 mole %, the procedure requiring in general several days. The initial temperature of the salt bath is about 250° C. (a point where the salt bath is molten).

The throughput is achieved in relation to the maximum salt bath temperature and maximum hot spot. The hot spot is determined by a probe through the center of the catalyst bed. The temperature of the salt bath can be adjusted to achieve the desired relationship between the conversion and flow rates of the n-$C_4$/air mixture (e.g. gas hourly space velocity - GHSV) . The flow rate is adjusted to conversion and the temperature relations given above.

The C, S and Y used in reporting reaction results have the following meaning and relationship C(conversion) x S(selectivity) =Y(yield); where:

$$\% \text{ Conversion} = \frac{\text{moles n-butane reacted}}{\text{moles n-butane fed}} \times 100$$

$$\% \text{ Selectivity} = \frac{\text{moles maleic anhydride produced}}{\text{moles n-butane reacted}} \times 100$$

The term "weight yield" means the amount of maleic anhydride produced from a given amount of n-butene, calculated as follows:

$$\text{wt yield} = \frac{98 \text{ (moles wt of maleic anhydride)}}{58 \text{ (mole wt of butane)}} \times \text{mole \% yield}$$

Percent crystallinity is determined by comparing the intensity of the 2.94d reflection of the dried catalyst material to that of a secondary standard of $VOHPO_4 \cdot \frac{1}{2} H_2O$.

The results from the testing of each of the samples are shown in TABLE I below. The activity comparisons are made at about the same conversion level (about 80%). The results indicate that by replacing the molybdenum trioxide with phosphomolybdic acid an improvement in the catalytic activity is observed. To obtain 80% conversion the catalyst prepared in comparative Example 1 required operating at lower productivity as indicated by the lower space velocity (2000 versus 2500 GHSV) and lower feed concentration of butane (0.97% versus 1.3%). Furthermore the catalyst in Example 1 required a higher salt bath temperature and had a higher hot spot temperature, both of which are not desirable in commercial operations.

TABLE I[(1)]

| EXAM. | HRS ON STM | TEMP. °C. BATH | TEMP. °C. HOT SPOT | n-BUTANE mole | GHSV hr−1 | CONV. mole % | SELEC mole % | YIELD wt % |
|---|---|---|---|---|---|---|---|---|
| 1 | 840 | 411 | 458 | 0.97 | 2000 | 80.4 | 66.4 | 90.4 |
| 2 | 843 | 375 | 421 | 1.30 | 2500 | 80.2 | 68.5 | 92.7 |
|   | 1100 | 373 | 413 | 1.33 | 2500 | 80.7 | 69.0 | 93.9 |
| 3 | 1079 | 382 | 420 | 1.33 | 2500 | 80.5 | 67.2 | 91.3 |

[(1)]1" × 5' Reactor; 3.5' bed with thermowell; 3/16" × 3/16" tablets with 1/16' hole in center.

The invention claimed is:

1. In a method for preparing a molybdenum containing phosphorus/vanadium mixed oxide oxidation catalyst comprising reducing vanadium in the +5 valence state in a substantially anhydrous organic medium to a valence of less than +5 and digesting said reduced vanadium and a modifier comprising molybdenum in concentrated phosphoric acid wherein the improvement comprises adding said molybdenum as a solution of molybdenum compound prior to said digesting.

2. A method for preparing a phosphorus/vanadium/zinc/lithium/molybdenum mixed oxide oxidation catalyst comprising the steps of:
  admixing a +5 valence vanadium compound with an organic solvent, contacting said mixture with gaseous HCl until the valence of vanadium is reduced to less than +5 at a temperature in the range of 35° to 60° C.,
  adding a zinc compound, a lithium compound and a solution of a molybdenum compound to said organic solvent containing said vanadium having a valence of less than +5,
  digesting said reduced vanadium, zinc compound, lithium compound and molybdenum compound in concentrated phosphoric acid of about 98 to 101% H3PO4 by a first reflux step,
  removing a first portion of said organic solvent from said digested mixture by distillation,
  digesting said organic solvent in a second reflux step,
  removing a second portion of said organic solvent from said digested mixture by distillation to form a slurry of mixed oxides and organic solvent,
  recovering a dried mixed oxide composition and heating said dried mixed oxide composition at a temperature in the range of 200° to 400° C. for a sufficient period to improve the catalytic properties of the composition.

3. The method according to claim 2 wherein said molybdenum compound is dissolved in an organic solvent.

4. The method according to claim 3 wherein said solvent is a mixture of methanol and isobutanol.

5. The method according to claim 4 wherein said molybdenum compound is phosphomolybdic acid.

6. The method according to claim 2 wherein said molybdenum compound is dissolved in water.

7. The method according to claim 6 wherein said molybdenum compound is phosphomolybdic acid.

8. The method according to claim 2 wherein said valence is reduced at a temperature in the range of 37 to 50° C.

9. The method according to claim 8 wherein said first reflux step is maintained for sufficient time to initiate crystallization.

10. The method according to claim 9 wherein said second reflux step is maintained for a sufficient time to complete crystallization.

11. The method according to claim 10 wherein said first portion comprises about 20-85% of said organic solvent.

12. The method according to claim 11 wherein said second portion comprises about 40-85% of remaining organic solvent.

13. A method for preparing a phosphorus/vanadium/zinc/lithium/molybdenum mixed oxide oxidation catalyst comprising the steps of:
  admixing a +5 valence vanadium compound with an organic solvent, contacting said mixture with gaseous HCl until the valence of vanadium is reduced to less than +5 at a temperature in the range of 35° to 60° C.,
  adding a zinc compound, a lithium compound to said organic solvent containing said vanadium having a valence of less than +5,
  digesting said reduced vanadium, zinc compound, lithium compound and molybdenum compound in concentrated phosphoric acid of about 98 to 101% H3PO4 by a first reflux step,
  removing a first portion of said organic solvent from said digested mixture by distillation,
  adding a solution of a molybdenum compound to said digested mixture,
  digesting said organic solvent in a second reflux step,
  removing a second portion of said organic solvent from said digested mixture by distillation to form a slurry of mixed oxides and organic solvent,
  recovering a dried mixed oxide composition and heating said dried mixed oxide composition at a temperature in the range of 200° to 400° C. for a sufficient period to improve the catalytic properties of the composition.

14. The method according to claim 13 wherein said molybdenum compound is dissolved in an organic solvent.

15. The method according to claim 14 wherein said solvent is a mixture of methanol and isobutanol.

16. The method according to claim 14 wherein said molybdenum compound is phosphomolybdic acid.

17. The method according to claim 13 wherein said molybdenum compound is dissolved in water.

18. The method according to claim 17 wherein said molybdenum compound is phosphomolybdic acid.

19. The method according to claim 13 wherein said valence is reduced at a temperature in the range of 37° to 50° C.

20. The method according to claim 19 wherein said first reflux step is maintained for sufficient time to initiate crystallization.

21. The method according to claim 20 wherein said second reflux step is maintained for a sufficient time to complete crystallization.

22. The method according to claim 21 wherein said first portion comprises about 20-85% of said organic solvent.

23. The method according to claim 22 wherein said second portion comprises about 40-85% of remaining organic solvent.

* * * * *